United States Patent [19]

Sato

[11] Patent Number: 4,545,369

[45] Date of Patent: Oct. 8, 1985

[54] WATERPROOF ENDOSCOPE

[75] Inventor: Mitsuru Sato, Tokyo, Japan

[73] Assignee: Kabushiki Kaisha Machida Seisakusho, Japan

[21] Appl. No.: 605,620

[22] Filed: Apr. 30, 1984

[30] Foreign Application Priority Data

May 18, 1983 [JP] Japan .................... 58-73070[U]

[51] Int. Cl.$^4$ ............................................. A61B 1/06
[52] U.S. Cl. .................................................. 128/4
[58] Field of Search ....................................... 128/4, 6

[56] References Cited

U.S. PATENT DOCUMENTS

| 4,216,767 | 8/1980 | Aoshiro | 128/6 |
| 4,241,729 | 12/1980 | Aoshiro | 128/4 |
| 4,341,205 | 7/1982 | Hosono et al. | 128/6 |
| 4,367,730 | 1/1983 | Tanaka | 128/6 |

Primary Examiner—William H. Grieb
Attorney, Agent, or Firm—Kane, Dalsimer, Kane, Sullivan and Kurucz

[57] ABSTRACT

A waterproof endoscope includes a insertion tube adapted to be inserted into a hollow organ. A hollow housing is connected to the insertion tube in an air-tight manner and disposed in communication therewith, the housing having an aperture formed therethrough. Mounted on the housing is a valve which includes a valve element for normally closing the aperture in the housing, and a spring made of a marmen alloy which is returned to a preselected shape at a predetermined temperature so as to urge the valve element away from the aperture, thereby opening the valve.

8 Claims, 8 Drawing Figures 4,545,369

WATERPROOF ENDOSCOPE

BACKGROUND OF THE INVENTION

1. Field of the Invention

This invention relates to an endoscope of the waterproof type.

2. Prior Art

Waterproof endoscopes comprises an insertion tube made of a relatively flexible material and has a free end adapted to be inserted into a hollow organ of a subject. Such a waterproof endoscope is entirely hermetically sealed, and is subjected to a sterilization at elevated temperatures in an atmosphere of ethylene oxide or the like. During this high temperature sterilization, the flexible insertion tube becomes softened due to the high temperature encountered, and the pressure in the endoscope is so increased that the flexible insertion tube is expanded or bulged and may finally be subjected to rupture.

SUMMARY OF THE INVENTION

It is therefore an object of this invention to provide a waterproof endoscope having means whereby the endoscope can be suitably prevented from being subjected to an excessive internal pressure, thereby protecting against the rupture of a insertion tube.

According to the present invention, there is provided a waterproof endoscope which comprises a insertion tube having one end adapted to be inserted into a hollow organ of a subject; control means connected to the insertion tube for controlling the operation of the insertion tube; a hollow housing connected to the insertion tube in an air-tight manner and disposed in communication therewith, the housing having an aperture formed therethrough; a guide tube connected to the control means at one end thereof; a plug member connected to the other end of the guide tube, the plug member being connectable to a source of light; an ocular tube connected to the inner tube; first optical means extending through the insertion tube, the hollow housing and the guide tube, the first optical means being connected to the plug member for supplying light to the one end of the insertion tube; second optical means extending from the one end of the insertion tube to the ocular tube; and valve means mounted on the hollow housing, the valve means including a valve element for normally closing the aperture of the housing, and a spring made of a marmen alloy which is returned to a preselected shape at a predetermined temperature so as to urge the valve element into its open position away from the aperture of the housing, thereby opening the valve means.

DESCRIPTION OF THE PREFERRED EMBODIMENT OF THE INVENTION

Figure 1:
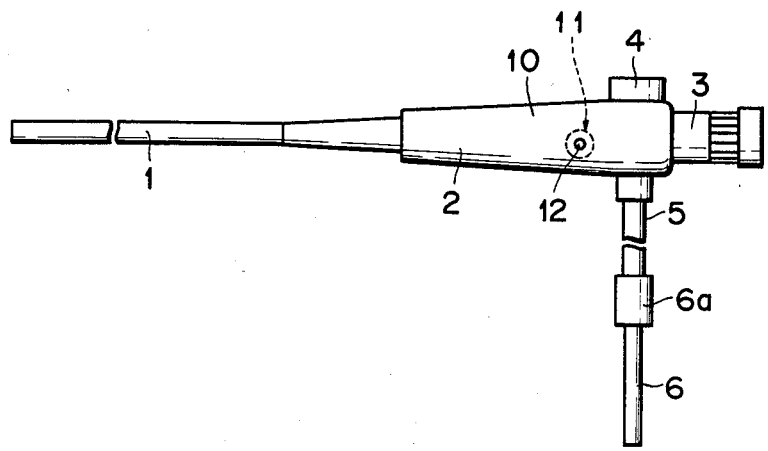
FIG. 1 is a side-elevational view of a waterproof endoscope provided in accordance with the present invention.

The invention will now be described with reference to the drawings in which like reference numerals designate corresponding parts in several views.

A waterproof endoscope shown in FIG. 1 broadly comprises a control unit 2, a flexible insertion tube 1 connected at one end thereof to the control unit 2, and a guide tube 5 extending from the control unit 2. The control unit 2 includes a hollow elongated housing 10 made of a rigid material, and an ocular tube 3 containing ocular lenses is connected to one end of the housing 10 remote from the flexible insertion tube 1. The insertion tube has a closed distal end on which an inspection window and a lighting window are provided, the distal end portion of the flexible insertion tube 1 being adapted to be inserted into a hollow organ of a subject. A plug member 6 includes a hollow cylindrical head portion 6a which is connected to one end of the guide tube 5 remote from the housing 10, the free end portion of the plug member 6 being adapted to be connected to a source of light (not shown). Although not shown in the drawings, a first bundle of optical fibers extends between the inspection window and the ocular tube 3 through the insertion tube 1 and the housing 10. Also, a second bundle of optical fibers extends between the lighting window and the plug member 6 through the insertion tube 1, the housing 2 and the guide tube 5. With this construction, light from the above-mentioned light source is applied to the lighting window, so that the hollow organ can be observed through the ocular tube 3.

A thumb nut 4 is rotatably mounted on the housing 10 and is operatively connected to a drum (not shown) rotatably mounted within the housing 10. An operating wire (not shown) extends between and connected at opposite ends thereof to the distal end of the flexible insertion tube 1 and the drum. Upon rotation of the thumb nut 4, the operating wire is wound around the drum, so that the distal end portion of the insertion tube 1 is caused to be flexed or bent. The insertion tube 1, the housing 10, the ocular tube 3, the thumb nut 4, the guide tube 5 and the plug member 6 are connected together in an air-tight manner to provide a waterproof construction.

Figure 2:
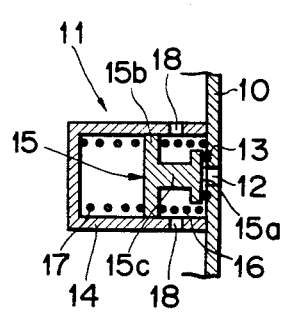
FIGS. 2 and 3 are cross-sectional views of a valve incorporated in the endoscope, showing its closed and open conditions, respectively.
Figure 3:
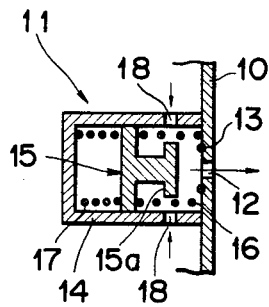

According to an important aspect of the present invention, a valve 11 is mounted within the housing 10 of the control unit 2, as best shown in FIGS. 2 and 3. An aperture 12 is formed through a peripheral wall of the housing 10. The valve 11 comprises a cylindrical valve body 14 having a closed and an open end. The valve body 14 is fixedly secured at its open end to the inner surface of the housing 10 in surrounding relation to the aperture 12. An annular seal element 13 in the form of an O ring is fixedly secured to the inner surface of the housing 10 and is disposed between the aperture 12 and the cylindrical valve body 14 in coaxial relation thereto. A valve element 15 is mounted within the cylindrical valve body 14 for movement along the axis thereof. The valve element 15 has a pair of first and second disc portions 15a and 15b and a connective portion 15c interconnecting these disc portions 15a, 15b, the disc portions 15a and 15b and the connective portion 15c being disposed coaxially with the valve body 14. The diameter of the second disc portion 15b is slightly smaller than the inner diameter of the cylindrical valve body 14 and disposed in sliding contact therewith. The first disc 15a is smaller in diameter than the second disc portion 15b. A return coil spring 17 acts between the closed end of the valve body 14 and the second disc portion 15b of the valve element 15 to normally urge the valve element 15 toward the aperture 12. A coil spring 16 is mounted around the first disc portion 15a and the connective portion 15c and acts between the inner surface of the housing 10 and the second disc portion 15b. The coil spring 16 is made of a marmen alloy having a shape memory effect, such as nitinol. The coil spring 16 of a marmen alloy is so processed that it is returned to a preselected shape when the ambient temperature reaches a predetermined level, for example, 60° C. In other words, the coil spring 16 of a marmen alloy is expanded axially into the preselected shape at the predetermined temperature. At room temperatures, the spring force of the return coil spring 17 is greater than that of the coil spring 16, so that the coil spring 17 urges the valve element 15 toward the aperture 12 with the first disc portion 15a held in sealing engagement with the seal element 13 to maintain the valve 11 in its closed condition, as shown in FIG. 2. The valve body 14 has holes 18 formed through the cylindrical wall thereof by which the housing 10 is in communication with the valve body 14. In the closed condition of the valve 11, the aperture 12 is closed by the valve element 15 so that the endoscope is maintained in an air-tight condition.

When the endoscope is sterilized at elevated temperatures in an atmosphere of ethylene oxide or the like, the valve 11 is opened to reduce an increased pressure in the endoscope. More specifically, when the temperature rises to the predetermined level during the high temperature sterilization, the contracted coil spring 16 of a marmen alloy is abruptly returned or expanded axially into its preselected shape so that it urges the valve element 15 toward the closed end of the valve body 14 against the bias of the return coil spring 17, with the first disc portion 15a moved away from the seal element 13, thereby opening the valve 11, as shown in FIG. 3. In this condition, the interior of the endoscope is caused to communicate with the exterior thereof through the holes 18 and the aperture 12. Thus, the flexible insertion tube 1 is prevented from expansion and rupture.

After the above high temperature sterilization, the force of the coil spring 16 is lowered when the temperature is decreased, so that the return spring 17 again urges the valve element 15 toward the aperture 12 to bring the first disc portion 15a into sealing engagement with the seal element 13. Thus, the endoscope is again maintained in an airtight manner.

Figure 4:
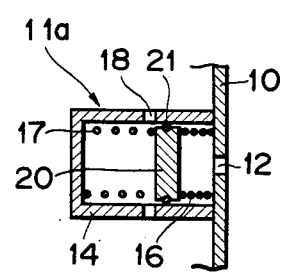
FIGS. 4 and 5 are views similar to FIGS. 2 and 3 but showing a modified valve.
Figure 5:
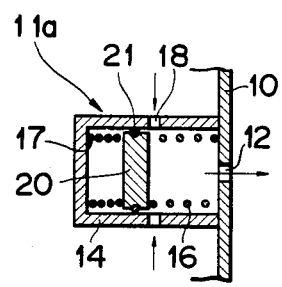

According to a modified form of the invention shown in FIGS. 4 and 5, the valve 11 is replaced by a valve 11a. The valve 11a differs from the valve 11 in that a disc-shaped valve element 20 is received within a cylindrical valve body 14. An annular seal element 21 in the form of an O ring is fixedly mounted around the disc-shaped valve element 20, the seal element 21 being held in sliding and sealing engagement with the inner cylindrical surface of the valve body 14. A coil spring 16 made of a marmen alloy acts between the inner surface of the housing 10 and one face of the disc-shaped valve element 20 while a return coil spring 17 acts between the closed end of the valve body 14 and the other face of the disc-shaped valve element 20. At room temperatures, the return coil spring 17 urges the valve element 20 toward an aperture 12. Holes 18 formed through the cylindrical wall of the valve body 14 are so positioned that when the coil spring 16 is in its contracted form, the holes 18 are disposed between the valve element 20 and the closed end of the valve body 14. Thus, in this condition, the holes 18 are not in communication with the aperture 12, thereby maintaining the valve 11a in its closed condition as shown in FIG. 4. As described above for the valve 11, when the temperature reaches a preselected level, the contracted coil spring 16 is abruptly expanded axially into its preselected shape so that it urges the valve element 20 to move beyond the holes 18 toward the closed end of the valve body 14 against the bias of the coil spring 17 to open the valve 11a as shown in FIG. 5, thereby reducing the increased internal pressure of the endoscope.

Figure 6:
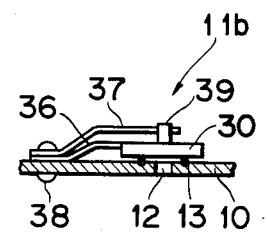
FIGS. 6 and 7 are views similar to FIGS. 2 and 3 but showing another modified valve.
Figure 7:
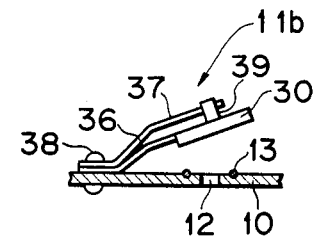

According to another modified form of the invention shown in FIGS. 6 and 7, the valve 11 is replaced by a valve 11b. The valve 11b comprises a first leaf spring 36 made of a marmen alloy and a second leaf spring 37, the leaf springs 36 and 37 being fixedly secured at their one ends to the inner surface of a housing 10 by a rivet 38. A valve element 30 is fixedly secured to the other end of the first leaf spring 36, and a contact piece 39 is fixedly secured to the other end of the second leaf spring 37 and held against the valve element 30. An annular seal element 13 in the form of an O ring is fixedly secured to the inner surface of the housing 10 in surrounding relation to an aperture 12 formed through the housing 10. At room temperatures, the spring force of the second leaf spring 37 is greater than that of the first leaf spring of a marmen alloy, so that the second leaf spring 37 urges the valve element 30 into sealing engagement with the seal element 13 to maintain the valve 11b in its closed condition as shown in FIG. 6. When the temperature rises to a predetermined temperature, the first leaf spring 36 is abruptly bent away from the aperture 12 into its preselected shape against the bias of the second leaf spring 37, so that the valve element 30 is brought out of engagement with the seal element 13 to open the valve 11b, as shown in FIG. 7.

Figure 8:
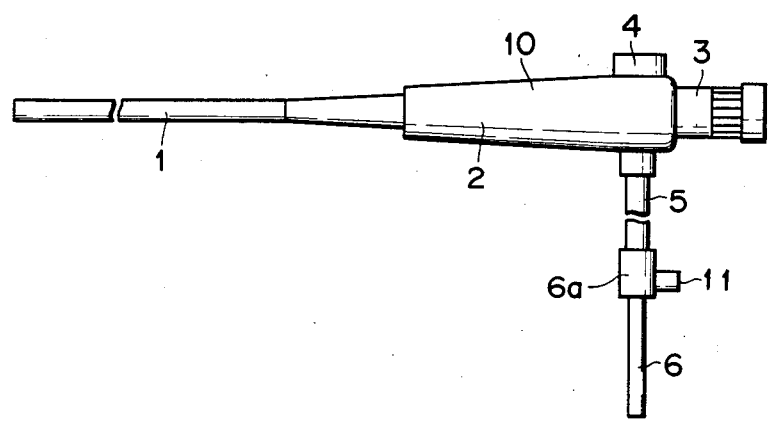
FIG. 8 is a view similar to FIG. 1 but showing a modified waterproof endoscope.

According to a further modified form of the invention, the valve 11 is mounted on the hollow head portion 6a of the plug member 6 as shown in FIG. 8.

While the endoscope according to the present invention has been specifically shown and described herein, the invention itself is not to be restricted by the exact showing of the drawings or the description thereof. For example, the spring of a marmen alloy may be so processed that it is alternately returned to two preselected shapes at room temperatures and elevated temperatures. In this case, the return spring is omitted. Also, the insertion to be may be formed of a rigid material.

What is claimed is:

1. A waterproof endoscope comprises:
   (a) a insertion tube having one end adapted to be inserted into a hollow organ of a subject;
   (b) control means connected to said insertion tube for controlling the operation of said insertion tube;
   (c) a hollow housing connected to said insertion tube in an air-tight manner and disposed in communication therewith, said housing having an aperture formed therethrough;
   (d) a guide tube connected to said control means at one end thereof;
   (e) a plug member connected to the other end of said guide tube, said plug member being connectable to a source of light;
   (f) an ocular tube connected to said insertion tube;

(g) first optical means extending through said insertion tube, said hollow housing and said guide tube, said first optical means being connected to said plug member for supplying light to said one end of said insertion tube;

(h) second optical means extending from said one end of said insertion tube to said ocular tube; and (i) valve means mounted on said housing, said valve means including a valve element for normally closing said aperture of said housing, and a spring made of a marmen alloy which is returned to a preselected shape at a predetermined temperature so as to urge said valve element away from said aperture, thereby opening said valve means.

2. A waterproof endoscope according to claim 1, in which said valve means comprises a return spring for normally urging said valve element to close said aperture against the bias of said spring of a marmen alloy, whereby said spring of a marmen alloy is returned to its preselected shape at the predetermined temperature to urge said valve element away from said aperture against the bias of said return spring.

3. A waterproof endoscope according to claim 2, in which said valve means comprises a hollow elongated valve body having an open and a closed end and secured at its open end to an inner surface of said housing in surrounding relation to said aperture, said valve body having a hole formed through a peripheral wall lying between its open and closed ends, said valve element being received in said valve body for movement along an axis thereof, said spring of a marmen alloy acting between the inner surface of said valve body and one side of said valve element while said return spring acts between said closed end of said valve body and the other side of said valve element, said hole being brought into communication with said aperture when said valve means is in its open condition.

4. A waterproof endoscope according to claim 3, in which said valve body is in the form of a cylinder, said valve element including a first disc portion, a second disc portion held in sliding contact with the inner cylindrical surface of said cylindrical valve body, and a connective portion interconnecting said first and second disc portions, said first disc portion being smaller in diameter than said second disc portion, said spring of a marmen alloy acting between the inner surface of said housing and said second disc portion, said return spring acting between said closed end of said valve body and said second disc portion, and said first disc portion being urged by said return spring to close said aperture when said valve means is in its closed condition.

5. A waterproof endoscope according to claim 3, in which said valve body is in the form of a cylinder, said valve element comprising a disc held at its periphery in sliding and sealing engagement with the inner cylindrical surface of said valve body, said spring of a marmen alloy acting between the inner surface of said housing and one face of said disc-shaped valve element while said return spring acts between said closed end of said valve body and the other face of the valve element, and said hole through said valve body being disposed between said valve element and said closed end of said valve body when said valve means is in its closed condition.

6. A waterproof endoscope according to claim 2, in which said spring of a marmen alloy and said return spring comprises leaf springs, respectively, which are secured at their one ends to the inner surface of said housing, said valve element being secured to the other end of said spring of a marmen alloy, and said return spring being held in engagement with said valve element.

7. A waterproof endoscope according to claim 1, in which said control means is mounted on said housing.

8. A waterproof endoscope according to claim 1, in which said housing is mounted on said plug member.

* * * * *